United States Patent

Shen et al.

[11] 4,126,442
[45] Nov. 21, 1978

[54] O-PHOSPHOROAMIDOPHENYLMORPHOLINE COMPOUNDS AND USE AS HERBICIDES

[75] Inventors: Kelvin K. Shen, Fountain Valley; Thomas S. Griffin, Orange, both of Calif.

[73] Assignee: United States Borax & Chemical Corp., Los Angeles, Calif.

[21] Appl. No.: 889,328

[22] Filed: Mar. 23, 1978

[51] Int. Cl.² ............................ C07F 9/65; A01N 9/36
[52] U.S. Cl. ................................................. 71/86; 71/87; 544/157
[58] Field of Search ...................... 544/157; 71/86, 87

[56] References Cited

U.S. PATENT DOCUMENTS 3,511,632  5/1970  Wollensak et al. .................... 71/86

OTHER PUBLICATIONS

Drach et al "Chem Abstracts," vol. 84 (1976), No. 43962s.

Primary Examiner—Henry R. Jiles
Assistant Examiner—R. W. Ramsuer
Attorney, Agent, or Firm—James R. Thornton

[57] ABSTRACT o-Phosphoroamidophenylmorpholines of the structure

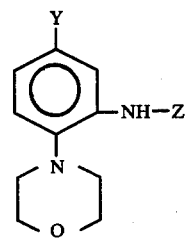

wherein Y represents a branched chain alkyl group of 3 to about 6 carbon atoms and z represents the group

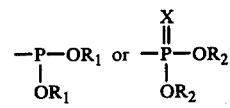

in which $R_1$ is lower alkyl, lower alkenyl, aralkyl or aryl, $R_2$ is hydrogen, lower alkyl, lower alkenyl, aralkyl or aryl, and X is O or S. The compounds are useful as herbicides and may be applied as a pre-emergence or post-emergence treatment to control unwanted plants.

13 Claims, No Drawings

O-PHOSPHOROAMIDOPHENYLMORPHOLINE COMPOUNDS AND USE AS HERBICIDES

RELATED APPLICATIONS

Shen et al., Ser. No. 766,289, filed Feb. 7, 1977, discloses and claims certain o-aminophenylmorpholines which are useful as intermediates for preparation of the compounds of the instant invention. Shen et al. application Ser. No. 802,606, filed June 2, 1977, discloses and claims o-amidophenylmorpholine and o-sulfamidophenylmorpholine compounds which are useful as herbicides.

SUMMARY OF THE INVENTION

This invention relates to a group of novel o-phosphoramidophenylmorpholines which are useful as herbicides. The compounds of the present invention may be represented by the formula

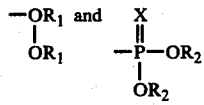

in which Y is a branched chain alkyl group of 3 to about 6 carbon atoms and Z is selected from the group consisting of $-\overset{OR_1}{\underset{OR_1}{|}}$ and $-\overset{X}{\underset{OR_2}{\overset{\|}{P}}-OR_2}$ wherein $R_1$ is selected from lower alkyl, lower alkenyl, aralkyl and aryl, $R_2$ is selected from hydrogen, lower alkyl, lower alkenyl, aralkyl and aryl, and X is selected from oxygen and sulfur. The lower alkyl and lower alkenyl groups which may be represented by $R_1$ and $R_2$ preferably contain up to about 6 carbon atoms and the aralkyl and aryl groups are preferably monocyclic aralkyl or aryl groups. Typical examples of such groups which may be represented by $R_1$ and $R_2$ include methyl, ethyl, isopropyl, n-butyl, n-hexyl, n-propyl, allyl, 2-butenyl, benzyl, phenylethyl, phenyl, and the like. The aromatic rings may also have substituents such as chloro, bromo, lower alkoxy, lower alkyl, etc. The branched chain alkyl groups which are represented by Y include isopropyl, tert.-butyl, sec.-pentyl, sec.-butyl, isoamyl, and the like. Preferably Y represents isopropyl or tert.-butyl.

The compounds are readily prepared by reaction of the corresponding phosphite, halophosphate, or halophosphite with an o-aminophenylmorpholine according to the equations:

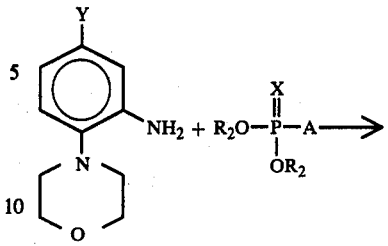

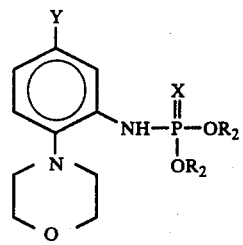

a)

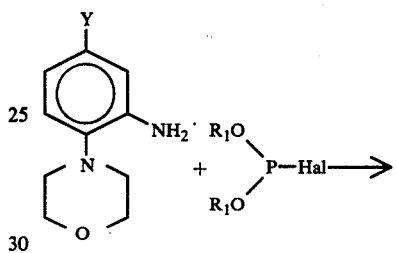

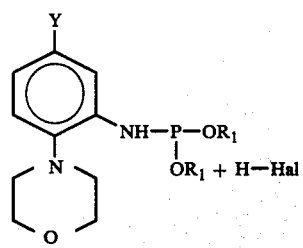

b)

in which A is H or a reactive halogen, Hal is a reactive halogen, and Y, X, $R_1$ and $R_2$ have the significance previously assigned except that $R_2$ may not be hydrogen. The reactions take place by combining about equimolar amounts of the reactants. In the case of (a), the reaction takes place in the presence of a catalyst such as triethylbenzylammonium chloride, aqueous sodium hydroxide, and a suitable solvent such as a halogenated hydrocarbon such as methylene dichloride. When A represents hydrogen in equation (a), tetrabromomethane is also included as a reactant. See A. Zwierzak, *Synthesis*, No. 8, pages 507–509 (1975) for typical reaction conditions. With reference to Equation (b), the reaction takes place in the presence of a tertiary amine such as triethylamine and a suitable solvent such as monoglyme. See Anderson et al., *J. Am. Chem. Soc.*, Vol. 74, pages 5304–5306 (1952) for a description of typical reaction conditions.

When $R_2$ represents hydrogen, the compounds may be prepared by catalytic reduction of a corresponding phosphoramidate according to the equation

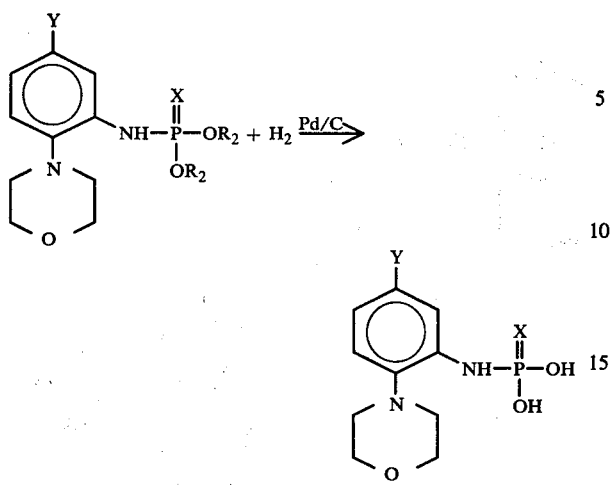

in which Y, X and $R_2$ have the significance previously assigned except $R_2$ does not represent hydrogen.

The desired products are crystalline solids or high boiling liquids and may be isolated by conventional procedures and purified by distillation under reduced pressure or recrystallization.

The intermediate o-aminophenylmorpholines may be prepared by catalytic reduction of the corresponding o-nitrophenylmorpholines as described by Nair et al., *J. Amer. Chem. Soc.*, Vol. 83, pages 3518–3521 (1961) and Shen et al. application Ser. No. 766,289 filed Feb. 7, 1977.

The following examples illustrate preparation of typical compounds of this invention.

EXAMPLE 1 diethyl N-(5-tert.-butyl-2-morpholinophenyl)phosphinate

To a stirred solution of 2.68 g. (17 mmoles) of diethyl chlorophosphite and 50 ml. of monoglyme was slowly added dropwise at ambient temperature a mixture of 4.0 g. (17 mmoles) of 4-(2-amino-4-tert.-butylphenyl)morpholine and 1.71 g. (5.1 mmoles) of triethylamine in 40 ml. of monoglyme. The resultant mixture was stirred at room temperature overnight and then filtered. The filtrate was evaporated to dryness under reduced pressure and the residue digested in a 4:1 mixture of n-hexane + methylene dichloride. The mother liquor was eluted with 99% methylene dichloride and 1% methanol through a silica gel column to give 0.3 g. of the product as a semi-solid.

EXAMPLE 2 dimethyl N-(5-isopropyl-2-morpholinophenyl)phosphoramidate

To a stirred solution of 10 ml. of methylene dichloride, 7 ml. of 20% aqueous sodium hydroxide, 3 g. of tetrabromomethane, and 0.2 g. of triethylbenzylammonium chloride was slowly added a solution of 4.0 g. (0.018 moles) of 4-(2-amino-4-isopropylphenyl)morpholine and 2.0 g. of dimethylphosphite dissolved in about 20 ml. of methylene dichloride. The reaction was exothermic and cooling by an ice bath was required. After stirring at ambient temperature for 18 hours, GC analysis indicated the reaction was about 30% complete. Accordingly, a 10% excess of the dimethylphosphite (0.2 g.) and an additional 0.3 g. of tetrabromomethane was added and stirring of the reaction mixture continued overnight. The mixture was then poured into an ice-water solution and the methylene dichloride layer separated. The aqueous layer was extracted twice with methylene dichloride and the combined methylene dichloride phases were rinsed thrice with water. After drying over anhydrous sodium sulfate, the methylene dichloride solution was filtered and evaporated under reduced pressure. The residue was eluted through a silica gel column using 99.5% methylene dichloride and 0.5% methanol to separate the product which was isolated from the solvent as a tan solid (2.2 g.; 37% yield); melting point 97°–98° C.

EXAMPLE 3

N-(5-tert.-butyl-2-morpholinophenyl)phosphoramidic acid

A solution of 1 g. of dibenzyl N-(5-tert.-butyl-2-morpholinophenyl) phosphoramidic acid dissolved in 100 ml. of dry methanol and 0.4 g. of palladium on carbon catalyst (wetted in monoglyme) was hydrogenated for ½ hour in a hydrogenation bottle. The resultant reaction mixture was filtered through Celite and the filtrate evaporated to dryness under reduced pressure. The product was obtained as a gray, crystalline solid residue (0.7 g.; 70% yield) melting at 79°–83° C.

EXAMPLES 4–17

The following are examples of other compounds according to the present invention which may be prepared by the above-described procedures.

4. dimethyl N-(5-tert.-butyl-2-morpholinophenyl)phosphoramidate, m. p. 120° C.
5. dimethyl N-(5-tert.-butyl-2-morpholinophenyl)thiophosphoramidate, m. p. 76°–77° C.
6. diethyl N-(5-tert.-butyl-2-morpholinophenyl)phosphoramidate, m. p. 68°–70° C.
7. dibenzyl N-(5-tert.-butyl-2-morpholinophenylphosphoramidate, m. p. 104°–105° C.
8. diphenyl N-(5-isopropyl-2-morpholinophenyl)phosphoramidate.
9. di-n-propyl N-(5-tert.-butyl-2-morpholinophenyl)phosphoramidate.
10. dibenzyl N-(5-sec.-butyl-2-morpholinophenyl)phosphoramidate.
11. diethyl N-(5-isopropyl-2-morpholinophenyl)thiophosphoramidate.
12. diallyl N-(5-tert.-butyl-2-morpholinophenyl)phosphoramidate.
13. dibenzyl N-(5-isopropyl-2-morpholinophenyl)thiophosphoramidate.
14. di-(4-chlorophenyl) N-(5-isopropyl-2-morpholinophenyl)phosphoramidate.
15. dimethyl N-(5-isoamyl-2-morpholinophenyl)phosphoramidate.
16. N-(5-isopropyl-2-morpholinophenyl)phosphoramidic acid.
17. diallyl N-(5-isopropyl-2-morpholinophenyl)thiophosphoramidate.

The compounds of this invention are useful as herbicides and can be applied as either a pre-emergence or post-emergence treatment; that is, they can be applied to soil in which the weeds will grow to kill or suppress the emergence of seedlings of undesirable plants or they can be applied to the foliage of the growing plants after emergence from the soil. Thus, the compounds can be used to control the growth of weeds by applying a phytotoxic amount of one or more of the active compounds of this invention to the locus to be protected; that is, soil in which the weeds are growing or will grow or the foliage of the growing plants. When used as a pre-emergence treatment, the compounds preferably are incorporated, such as by mixing into the top 1 to 3 inches of the soil, prior to planting the crop. When used as a post-emergence treatment, it is preferred that a directed spray by employed, thereby directing the application of the herbicide onto the foliage of the weeds and away from the foliage of the crop plants. Weeds, as used herein, is meant to include any plant growth which is undesirable.

The compounds are especially useful as pre-emergence herbicides with incorporation for selectively controlling weeds in the presence of desirable crops such as peanuts, corn and cotton. The weeds controlled include many of the broadleaf and grassy weeds such as jimsonweed, lambsquarter, mustard, pigweed, velvetleaf, wild oats, cocklebur, ragweed, nightshade, etc.

Generally, an application rate of from about 0.5 to about 10 pounds of one or more of the active compounds per acre is effective in controlling weed growth. Preferably, an application rate in the range of about 0.5 to 3 pounds per acre is used as a pre-emergence treatment. Slightly higher rates are usually required for a post-emergence treatment.

The following examples illustrate the herbicidal activity of representative compounds of this invention.

EXAMPLE 18

The compounds to be tested were evaluated as both a pre-emergent and post-emergent treatment. Greenhouse pots were planted to soybeans (SO), velvetleaf (VL), oats (O) and millet (M). The pots were sprayed on the same day as planting with an ethanol solution of the compound to be tested at a rate of 5 pounds per acre. Another set of pots with the same plants was treated after the plants had emerged and were about one inch in height. These pots were also sprayed with the solution of the compound to be tested at a rate of 5 pounds per acre. The pots were kept in the greenhouse and watered when needed. Twenty-one days after treatment, the pots were examined and the plants rated for herbicidal activity on a 0-9 scale in which 0 = no effect
1 = <10% injury
2 = 10-40% injury
3 = 40-70% injury
4 = >70% injury
5 = <25% kill
6 = 25-50% kill
7 = 50-75% kill
8 = 75-99% kill
9 = 100% kill The results are shown in Table I.

TABLE I

| Compound | Herbicidal Activity | | | | | | | |
|---|---|---|---|---|---|---|---|---|
| | Pre | | | | Post | | | |
| | SO | VL | O | M | SO | VL | O | M |
| Example 1 | 2 | 9 | 5 | 9 | 9 | 9 | 8 | 9 |
| Example 2 | 4 | 9 | 7 | 8 | 9 | 9 | 9 | 9 |
| Example 3 | 3 | 9 | 5 | 9 | 9 | 9 | 9 | 9 |
| Example 4 | 8 | 9 | 7 | 8 | 9 | 9 | 9 | 8 |
| Example 5 | 3 | 9 | 2 | 8 | 7 | 5 | 5 | 5 |
| Example 6 | 5 | 9 | 5 | 5 | 5 | 9 | 7 | 7 |

TABLE I-continued

| Compound | Herbicidal Activity | | | | | | | |
|---|---|---|---|---|---|---|---|---|
| | Pre | | | | Post | | | |
| | SO | VL | O | M | SO | VL | O | M |
| Example 7 | 1 | 8 | 0 | 5 | 9 | 9 | 5 | 5 |

EXAMPLE 19

Dimethyl N-(5-tert.-butyl-2-morpholinophenyl)phosphoramidate was evaluated as a pre-emergence herbicide in greenhouse tests with a broad group of crops and weeds at 1 and 2 pounds per acre. An ethanol solution of the compound was sprayed onto the soil and mixed into the top 1 inch thereof. Immediately thereafter, crops and weeds were planted in the treated soil at a depth of 0.5 inch. The flats were kept in the greenhouse and watered as needed. Twenty-eight days after treatment, the plants were rated on a 0 to 9 scale as described in Example 18. Where two numbers are used, i.e. 8/4, the first number represents the percent kill and the second number is the injury to the remaining plants. The results are given in Table II and are an average of two replicates.

TABLE II

| Plants | Herbicide Activity | |
|---|---|---|
| | 1 lb/A | 2 lb/A |
| corn | 0/1 | 0/1 |
| cotton | 0/1 | 0/2 |
| dry beans | 8/2 | 9 |
| peanuts | 0 | 0/1 |
| rice | 8/3 | 9 |
| soybeans | 0/1 | 6/1 |
| wheat | 7/2 | 9 |
| alfalfa | 9 | 9 |
| cocklebur | 6/2 | 8/3 |
| jimsonweed | 9 | 9 |
| lambsquarters | 9 | 9 |
| morningglory | 0/1 | 0/1 |
| mustard | 8/4 | 9 |
| prickly sida | 5/1 | 8/3 |
| pigweed | 8/4 | 9 |
| sesbania | 0 | 5/2 |
| velvetleaf | 8/3 | 9 |
| barnyard grass | 0/1 | 5/2 |
| foxtail | 0/2 | 8/2 |
| Johnsongrass | 0/1 | 8/2 |
| wild oats | 7/1 | 8/2 |
| ragweed | 8/1 | 9 |
| nightshade | 8/4 | 9 |

Since a relatively small amount of one or more of the active compounds should be uniformly distributed over the area to be treated, the compounds preferably are formulated with conventional herbicide carriers, either liquid or solid. Thus, the compounds can be impregnated on or admixed with a pulverulent solid carrier such as lime, talc, clay, Bentonite, calcium chloride, vermiculite, and the like. Alternatively, the compounds can be dissolved or suspended in a liquid carrier such as water, kerosene, alcohols, diesel oil, mineral oil, xylene, benzene, glycols, ketones and the like.

A surfactant is preferably included to aid in dispersion, emulsification and coverage. The surfactant can be ionic or non-ionic and may be liquid or a solid. The use of the term "surfactant" herein is intended to include such compounds commonly referred to as wetting agents, dispersing agents and emulsifying agents. Typical surfactants include the alkylarylsulfonates, the fatty alcohol sulfates, sodium salt of naphthalenesulfonic acid, alkylaryl polyether alcohols, long chain quaternary ammonium compounds, sodium salts of petroleum-derived alkylsulfonic acids, organophosphates, polyoxyethylene-sorbitan monolaurate, and the like. These dispersing and wetting agents are sold under numerous trademarks and may either be pure compounds, mixtures of compounds of the same general group, or they can be mixtures of compounds of different classes. Surfactants can also be included in compositions containing a solid inert carrier.

Concentrated compositions containing the active agent which can be subsequently diluted, as with water, to the desired concentration for application to plants and soil are also provided. The advantages of such concentrates are that they are prepared by the manufacturer in a form such that the user need only mix them with a locally available carrier, preferably water, thereby keeping shipping costs to a minimum while providing a product which can be used with a minimum of equipment and effort. Such concentrates may contain from about 5 to about 95 percent by weight of one or more of the active compounds with a carrier or diluent, which may be a liquid or a solid. Liquid carriers in which the active agent is soluble or other liquids in which the compound may be suspended or dispersed, can be used. A surfactant is also generally included to facilitate such dilution or dispersion in water. However, the surfactant itself may comprise the carrier in such concentrates.

The herbicidal compositions can include other beneficial adjuvants, such as humectants, oils and contact agents. Further, other herbicides such as the chlorophenoxyacetic acids, substituted uracils and ureas, dinitroanilines, phenylenediamines, thiocarbamates, carbamates, anilides, amides, and haloalkanoic acids, can be included in the formulation, if desired.

Various changes and modifications of the invention can be made, and, to the extent that such variations incorporate the spirit of this invention, they are intended to be included within the scope of the appended claims.

What is claimed is:

1. A compound of the formula

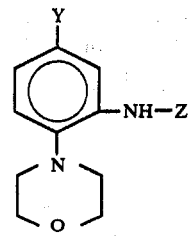

in which Y represents a branched chain alkyl group of 3 to about 6 carbon atoms and Z represents a group selected from

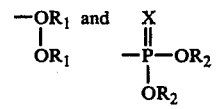

in which $R_1$ is selected from lower alkyl, lower alkenyl, aralkyl, and aryl, $R_2$ is selected from hydrogen, lower alkyl, lower alkenyl, aralkyl and aryl, wherein said aralkyl and aryl are selected from benzyl, phenylethyl, phenyl and the chloro, bromo, loweralkoxy and loweralkyl ring substituted derivatives thereof, and X is O or S.

2. A compound according to claim 1 in which $R_1$ is lower alkyl.

3. A compound according to claim 1 in which $R_2$ is lower alkyl.

4. A compound according to claim 1 in which $R_2$ is hydrogen and X is O.

5. A compound according to claim 1 in which Y is tert.-butyl.

6. A compound according to claim 1 in which Y is isopropyl.

7. A herbicidal composition comprising a phytotoxic amount of a compound according to claim 1, a surfactant and an inert carrier therefor.

8. The method of controlling weed growth which comprises applying a phytotoxic amount of a compound according to claim 1 to the locus of said weeds.

9. The method according to claim 8 in which $R_1$ and $R_2$ are lower alkyl.

10. The method according to claim 8 in which X is O.

11. The method according to claim 8 in which said compound is applied as a pre-emergence treatment and incorporated in the soil.

12. The method according to claim 11 in which about 0.5 to 3 pounds of said compound is applied per acre.

13. The method according to claim 8 in which said compound is dimethyl N-(5-tert.-butyl-2-morpholinophenyl)phosphoramidate.

* * * * *

UNITED STATES PATENT OFFICE
CERTIFICATE OF CORRECTION

Patent No. 4,126,442  Dated November 21, 1978

Inventor(s) Kelvin K. Shen & Thomas S. Griffin

It is certified that error appears in the above-identified patent and that said Letters Patent are hereby corrected as shown below:

In Column 1, Line 40, delete " $\begin{matrix} -OR_1 \\ | \\ OR_1 \end{matrix}$ " and insert -- $\begin{matrix} -P-OR_1 \\ | \\ OR_1 \end{matrix}$ --

In Column 8, Lines 15-20, delete " $\begin{matrix} -OR_1 \\ | \\ OR_1 \end{matrix}$ " and insert -- $\begin{matrix} -P-OR_1 \\ | \\ OR_1 \end{matrix}$ --

Signed and Sealed this

Twenty-seventh Day of March 1979

[SEAL]

Attest:

RUTH C. MASON
Attesting Officer

DONALD W. BANNER
Commissioner of Patents and Trademarks